Jan. 2, 1962 L. A. LAMBOROT Plant Pat. 2,117
CHRYSANTHEMUM PLANT
Filed March 30, 1960
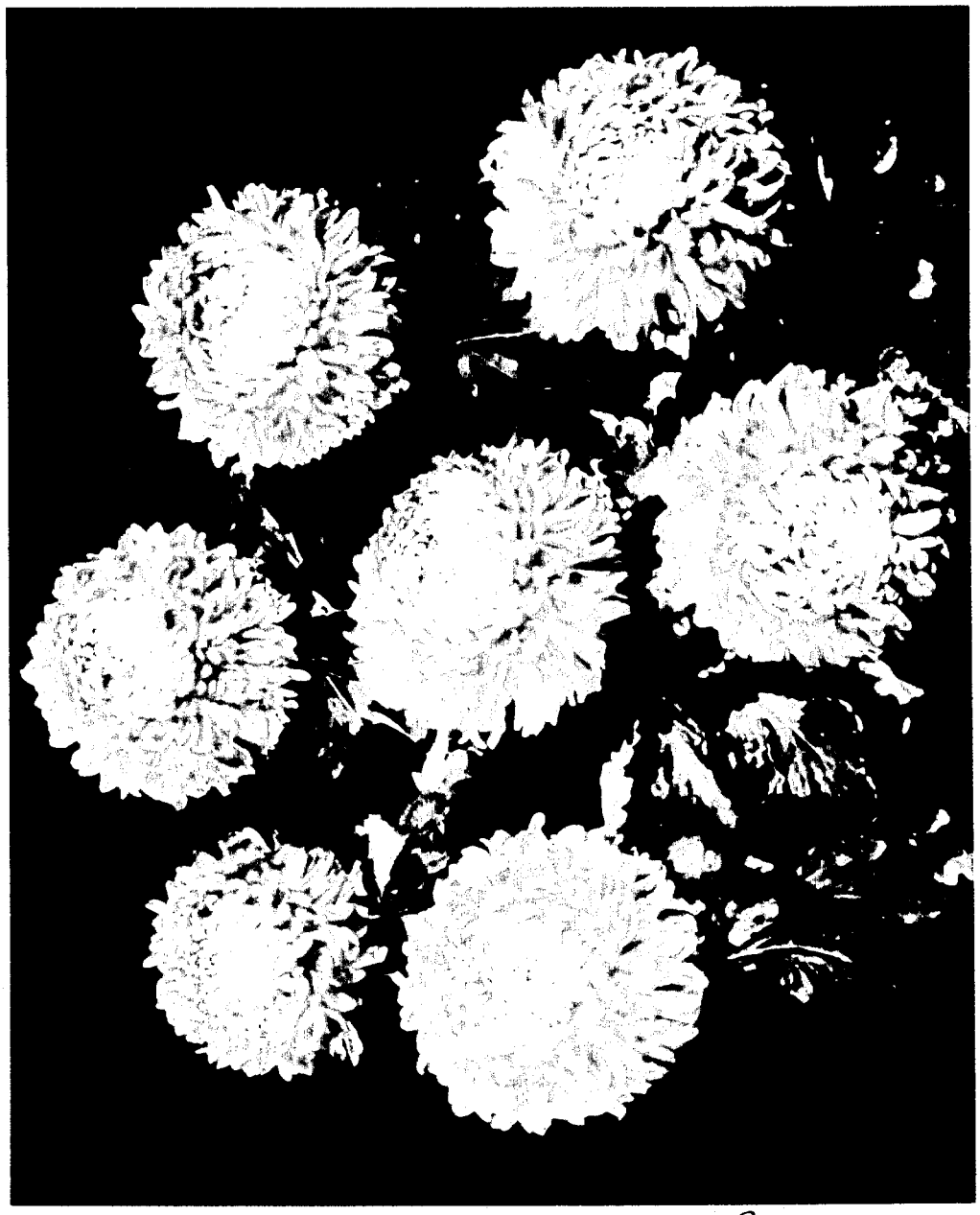
Inventor
L. A. Lamborot
by Robb & Robb
attorneys United States Patent Office Plant Pat. 2,117
Patented Jan. 2, 1962

2,117
CHRYSANTHEMUM PLANT

Lazare Antoine Lamborot, Montceau les Mines, France, assignor to George J. Ball, Inc., West Chicago, Ill., a corporation of Illinois Filed Mar. 30, 1960, Ser. No. 18,792
1 Claim. (Cl. 47—60)

My present invention comprises a new and distinct variety of chrysanthemum plant, which is a seedling produced as a result of crossing the variety "P G" (unpatented), which is a variety of my own production, with another variety of my own production, which I have designated as 55–53, and likewise unpatented.

The object of this invention has been to produce a new variety of chrysanthemum plant of the *morifolium* type, which will comprise an improvement in the pot chrysanthemum trade, some of the features of improvement being to develop a bloom whose center will always be closed even at maturity, whose stems will break properly and cleanly after the pinch, and will have brighter color blooms and be more compact with strong stems.

This present new variety is one of several which I have developed in an extensive program of careful selection and cross-breeding of various chrysanthemum varieties, to develop more showy, bright blooms, with stronger stems and more uniform habit of growth than known, widely produced varieties.

The result of the specific hybridization previously mentioned, has been to produce my present new and distinct variety of chrysanthemum plant, characterized by the very large, closed, high center and strong reddish orange shaded to a slightly redder hue of reddish orange color of its blooms, the very double arrangement of its petals, its shorter, stronger, more uniform length stems, its better more compact habit, and profuse though intermittent mid-season blooming period.

More specifically, the blooms of my new variety appear to have a general tonality from a distance, of a strong reddish orange shaded to a slightly redder hue of reddish orange color (Nickerson Color Fan, published by Munsell Color Company).

As grown in the vicinity of Montceau les Mines, France, under conditions of uniform culture, the plants of my new variety have grown in more uniform, compact bushes, with abundant, large foliage.

My new variety appears to have numerous characteristics of the parent varieties, but better characteristics than either separately, and my new variety differs from both its parents and from other known varieties in many respects.

The commercial pot chrysanthemum trade in the United States, includes three so called bronze varieties (all unpatented), which are probably most important, known as "Delaware," "Woking Scarlet" and "Calypso Bronze."

I believe my new variety constitutes an improvement over the variety "Delaware" for the reason that the bloom of "Delaware" shows an open center upon maturity, whereas my new variety does not. Further my new variety breaks more freely or properly after the pinch in contrast to "Delaware," which does not. The color of my new variety is much brighter, that of "Delaware" being more nearly a dark red.

The variety "Woking Scarlet" has a tendency to grow to extreme height, whereas my new variety is more uniformly shorter. Furthermore my new variety produces blooms which are at least fifty percent (50%) larger than "Woking Scarlet." This latter variety also tends to break poorly after the pinch, unlike my new variety, which breaks cleanly.

In comparing my new variety to "Calypso Bronze," it is noted that the latter is not nearly as showy and bright, the plant having a tendency to produce weak stems, which provide a sloppy, unsightly plant. Furthermore the blooms of "Calypso Bronze" are much smaller than those of my new variety.

In view of the foregoing, the substantial improvement provided by my new variety is emphasized and important for commercial as well as patentable reasons.

Under the conditions of culture previously related, which have been undertaken in the vicinity of Montceau les Mines, France, plants of my new variety have shown vigorous growth, somewhat more compact form and slightly more than dwarf size than similar varieties.

My new variety has been asexually reproduced by cuttings in the vicinity of Montceau les Mines, France, and found to retain its distinctive characteristics through such reproduction.

The accompanying drawing forming a part hereof, shows a typical plant of my new variety of chrysanthemum.

The following is a detailed description of my new variety of chrysanthemum plant, the color references being to the Nickerson Color Fan published by the Munsell Color Company:

*Description*

Parentage: Seedling.
*Seed parent.*—"P G" (unpatented).
*Pollen Parent.*—55–53 (unpatented).
Classification: Botanic—*Chrysanthemum morifolium.*

*Flower*

Blooming habit: Blooms profusely, intermittently in mid-fall.

Bud:
*Size.*—Large.
*Form.*—Short with flat top. Not affected by hot or wet weather.
*Color.*—When sepals first divide—between 7.5YR 8/8, moderate orange yellow, and 7.5YR 7/11, strong orange yellow. When petals begin to unfurl—7.5YR 8/8, moderate orange yellow. When half blown, inside of petals—between 5R 5/13, vivid red, and 5R 4/12, strong red. When half blown; reverse of petals—2.5YR 7/10, strong orange.
*Sepals.*—Stand up.
*Calyx.* — Shape — funnel. Size — small. Aspect—mossy. Odor when rubbed—typical chrysanthemum odor.
*Peduncle.* — Length — short. Aspect — rough. Color — medium green. Strength — stiff. Bud opens well and is not affected by adverse conditions.

Bloom:
*Size.*—Very large. Average size when fully expanded 5½ inches.
*Borne.*—In clusters unless disbudded and flat.
*Stems.*—Short, strong.
*Form.*—When first open—high center. Permanence—retains its form to the end. Fashion—like a show dahlia.
*Petalage.*—Very double. Number of petals too numerous to count.
*Color.*—Center of flower—2.5YR 7/10, strong orange washed with 2.5YR 8/6, light orange. Outer petals—7.5R 5/13, strong reddish orange washed with 5R 5/13 vivid red. Base of petals (singlet)—between 5R 4/12 strong red and 5R 3/7, dark red. Inside of petals—7.5R 5/13, strong reddish orange, washed with 5R 5/13 vivid red. Reverse of petals—2.5YR 7/10, strong orange washed with 2.5YR 8/6, light orange. General tonality from a distance—10R 5/11, strong reddish orange, shaded with 7.5R 5/13, strong reddish orange.

*Discoloration.*—General tonality at end of: first week—between 7.5R 6/12, strong reddish orange and 7.5R 5/13, strong reddish orange; second week—between 10R 5/11 and 10R 6/11 strong reddish orange; third week—between 7.5R 6/12 and 10R 6/12 strong reddish orange.

Petals:

*Texture.*—Thick. Not affected by hot or wet weather.

*Appearance.*—Inside—satiny. Outside—satiny.

*Form.*—Oval.

*Arrangement.*—Imbricated.

*Petaloids in center.*—Many.

*Persistance.*—Hang on and dry.

*Fragrance.*—Normal chrysanthemum odor.

*Lastingness.*—On the plant—very long. As cut flower—very long.

Genital organs:

*Stamens, anthers.* — Small. Color — yellow. Arrangement—regular around styles.

*Stamens, filaments (threads).* — Short. Color — lemon yellow.

*Pollen.*—Lemon yellow.

*Styles.*—Columnar.

*Stigmas.*—Color—yellow.

*Ovaries.*—All enclosed in calyx.

Fruit: Variety is sterile with its own pollen.

*Form.*—Seeds protruding.

*Aspect.*—Rough.

*Color at maturity.*—Russet brown.

*Sepals.*—Caducous.

*Plant*

Form: Bush.

Growth: Compact.

Foliage:

*Leaflets.*—One (alternate).

*Size.*—Large.

*Quantity.*—Abundant.

*Color.*—New foliage: upper side—light green; under side—light green.

*Shape.*—Lanceloate.

*Texture.*—Upper side—smooth.

*Ribs and veins.*—Ordinary.

*Edge.*—Undulated.

*Serration.*—Single.

*Leaf stem.*—Color—green. Under side—rough.

*Stipules.*—Medium.

Immune to diseases.

Wood (new):

*Color.*—Light green.

*Bark.*—Smooth.

Wood (old):

*Color.*—Green.

*Bark.*—Rough.

I claim:

A new and distinct variety of chrysanthemum plant substantially as herein disclosed, characterized as to novelty by the very large, closed, high center and strong reddish orange shaded to a slightly redder hue of reddish orange color of its blooms, the very double arrangement of its petals, its shorter, stronger, more uniform length stems, and its better, more compact habit and profuse quantity of blooms.

No references cited.